(12) United States Patent
Wang et al.

(10) Patent No.: US 8,895,725 B2
(45) Date of Patent: Nov. 25, 2014

(54) USE OF 9, 10-ANTHRAQUINONE COMPOUNDS

(75) Inventors: Shuguang Wang, Shanghai (CN); Jin Zhong, Shanghai (CN); Deyun Kong, Shanghai (CN); Jue Hu, Shanghai (CN); Bo Li, Shanghai (CN); Wen Gao, Shanghai (CN); Chunyan Gai, Shanghai (CN); Changlong Zhuang, Shanghai (CN); Haitao Mao, Shanghai (CN)

(73) Assignees: Shanghai Institute of Pharmaceutical Industry, Shanghai (CN); Institute Pasteur of Shanghai, Chinese Academy of Sciences, Shanghai (CN)

( * ) Notice: Subject to any disclaimer, the term of this patent is extended or adjusted under 35 U.S.C. 154(b) by 200 days.

(21) Appl. No.: 13/130,130

(22) PCT Filed: Nov. 23, 2009

(86) PCT No.: PCT/CN2009/075075
§ 371 (c)(1),
(2), (4) Date: May 19, 2011

(87) PCT Pub. No.: WO2010/057443
PCT Pub. Date: May 27, 2010

(65) Prior Publication Data
US 2011/0224414 A1    Sep. 15, 2011

(30) Foreign Application Priority Data
Nov. 21, 2008  (CN) .......................... 2008 1 02031121

(51) Int. Cl.
| | |
|---|---|
| *A61K 31/192* | (2006.01) |
| *C09B 1/473* | (2006.01) |
| *A61K 36/708* | (2006.01) |
| *A61K 36/74* | (2006.01) |
| *A61K 31/185* | (2006.01) |
| *A61K 31/704* | (2006.01) |
| *A61K 31/122* | (2006.01) |
| *A61K 31/7004* | (2006.01) |
| *A61K 36/482* | (2006.01) |

(52) U.S. Cl.
CPC ............. *A61K 31/122* (2013.01); *A61K 36/708* (2013.01); *A61K 31/192* (2013.01); *A61K 36/74* (2013.01); *A61K 31/185* (2013.01); *A61K 31/704* (2013.01); *A61K 31/7004* (2013.01); *A61K 36/482* (2013.01)
USPC .......... 536/124; 536/6.4; 548/300.4; 552/208

(58) Field of Classification Search
CPC ....................................................... C09B 1/473
USPC .................. 536/124, 6.4; 548/300.4; 552/208
See application file for complete search history.

(56) References Cited

FOREIGN PATENT DOCUMENTS

WO    WO 2008060695 A2 *  5/2008
WO    WO 2008097112 A1 *  8/2008

* cited by examiner

*Primary Examiner* — Patrick Lewis
*Assistant Examiner* — Everett White
(74) *Attorney, Agent, or Firm* — Lowe Hauptman & Ham, LLP

(57) ABSTRACT

Use of 9,10-anthraquinone compounds of formula (I) or pharmaceutical salts thereof or plant extracts containing said compounds in the preparation of anti-HCV medicaments is disclosed, in which $Y^1$ are $Y^2$ are independently hydrogen, hydroxyl or groups of formula (II); and $R^1$, $R^2$, $R^3$, $R^4$, $R^5$ and $R^6$ are independently hydrogen, hydroxyl, carboxyl, cyano group, nitro group, groups of formula (III) or groups selected from those substituted or unsubstituted groups: amino, $C_1$-$C_6$ aliphatic hydrocarbon, $C_3$-$C_7$ cyclic aliphatic hydrocarbon, $C_1$-$C_6$ alkoxy, $C_2$-$C_7$ carbalkoxy, $C_1$-$C_4$ acyloxy, $C_6$-$C_{20}$ aryl, or 5 to 7 members heterocyclic or benzoheterocyclic thereof; or $R_5$ and $R_6$ form the group of formula (IV). The compounds of present invention are cheap, safe and effective because that they mostly come from traditional Chinese medicines and have better anti-HCV effects and lighter side effects.

12 Claims, No Drawings

USE OF 9,10-ANTHRAQUINONE COMPOUNDS

RELATED APPLICATIONS

The present application is National Phase of PCT/CN2009/075075 filed Nov. 23, 2009, and claims priority from, Chinese Application Number 200810203112.1 filed Nov. 21, 2008.

FIELD OF THE INVENTION

The present invention relates to the use of 9,10-anthraquinone compounds, especially the use of 9,10-anthraquinone compounds in the preparation of anti-hepatitis C virus medicaments.

BACKGROUND OF THE INVENTION

According to incomplete statistics, hepatitis C antibody positive, patients amount to 40,000,000 at present in China and 80% of them will suffer from chronic hepatitis C. Hepatitis C is a kind of liver disease transmitting by way of blood, sexual contact, mother-baby and daily contact et al. After infecting of HCV, like HBV the sufferer is likely to catch chronic hepatitis, liver cirrhosis and liver cancer.

At present, long-acting interferon combined with Ribavirin is mainly used to treat patients with hepatitis C virus whose liver function is normal and the overall sustained virological response rate is 52%. But during the process of treatment using interferon and Ribavirin, the adverse reactions of bone marrow suppression, depression and digestive tract symptom et al. may appear. Moreover, long-acting interferon is expensive and the cost of a course of 48 weeks is about ¥60,000. Consequently, it is a focus in pharmaceutical industry at the present time to develop natural drugs that have better anti-HCV efficacy with lower price and little side effects.

SUMMARY OF THE INVENTION

It is a technical problem to be solved by the present invention to provide a medicine for anti-hepatitis C virus that has better curative effect, is lower in price and has little side effects. So the use of 9,10-anthraquinone compounds (Formula I) in the preparation of anti-hepatitis C virus medicament is disclosed in this invention.

The use of 9,10-anthraquinone compound (Formula I), or pharmaceutically acceptable salt thereof, or plant extract containing said compound in the preparation of anti-hepatitis C virus medicament is disclosed in this invention.

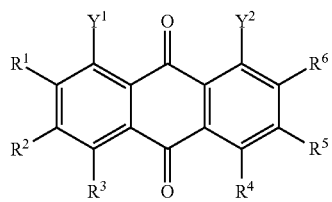

Formula I

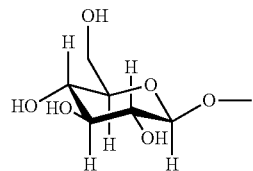

Formula II

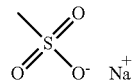

Formula III

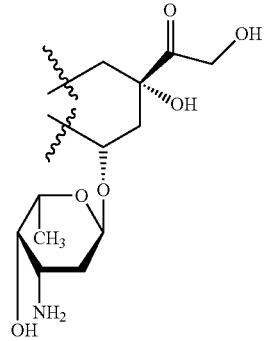

Formula IV

Wherein, $Y^1$ and $Y^2$ are independently hydrogen, hydroxyl or group as shown in Formula II; $R^1$, $R^2$, $R^3$, $R^4$, $R^5$ and $R^6$ are independently hydrogen, hydroxyl, carboxyl, cyano, nitryl, group as shown in Formula III or the following groups with substituent group/groups or unsubstituted: amino, $C_1$~$C_6$ chain hydrocarbyl, $C_3$~$C_7$ cyclic aliphatic hydrocarbyl, $C_1$~$C_6$ alkoxy, $C_2$~$C_7$ alkoxy carbonyl, $C_1$~$C_4$ acyloxy, $C_6$~$C_{70}$ aryl or 5~7 members heterocyclic ring or benzoheterocyclic ring thereof.

Preferably, $Y^1$ and $Y^2$ are hydroxyl; $R^1$, $R^2$, $R^3$, $R^4$, $R^5$ and $R^6$ are independently hydrogen, hydroxyl, carboxyl, cyano, nitryl, or the following groups with substituent group/groups or unsubstituted: amino, $C_1$~$C_6$ chain hydrocarbyl, $C_3$~$C_7$ cyclic aliphatic hydrocarbyl, $C_1$~$C_6$ alkoxy, $C_7$~$C_7$ alkoxy carbonyl, $C_1$~$C_4$ acyloxy, $C_6$~$C_{20}$ aryl or 5~7 members heterocyclic ring or benzoheterocyclic ring thereof.

Wherein, the said substituent group/groups is/are preferably one or more selected from the group consisting of halogen, $C_1$~$C_6$ chain hydrocarbyl, cyano, nitryl, amino, hydroxyl, carboxyl, $C_1$~$C_4$ alkoxy, mercapto, acyloxy and $C_6$~$C_{20}$ aryl; or $R^5$ and $R^6$ form a ring shown as Formula IV.

Wherein, the said 5~7 members heterocyclic ring is preferably the one that contains 1~3 hetero atom/atoms selected from the group consisting of oxygen, sulfur and nitrogen; the said $C_6$~$C_{20}$ aryl is preferably phenyl, naphthyl, tetrahydro naphthyl, 2,3-dihydro indenyl, diphenyl, phenanthryl, anthryl or acenaphthenyl.

More preferably, the said $R^1$, $R^2$, $R^3$, $R^4$, $R^5$ and $R^6$ are independently H, $CH_3$, OH, $OCH_3$, $OC_2H_5$, COOH, $COOCH_3$, $COOC_2H_5$, $CH_2OH$, trifluoromethyl, trifluoromethoxy or benzyl. Unless otherwise indicated, the following terms that are present in the description and the claims have the following meanings:

The term "chain hydrocarbyl" means branched or linear, saturated or unsaturated chain aliphatic hydrocarbyl group that has the indicated number of carbon atom/atoms.

The term "cyclic aliphatic hydrocarbyl" means branched or linear, saturated or unsaturated cyclic aliphatic hydrocarbon group that has the indicated number of carbon atom/atoms.

The term "alkoxy" means cyclic or acyclic alkyl that has the indicated number of carbon atom/atoms and is linked by an oxygen-bridge.

The term "halogen" means fluorine, chlorine, bromine or iodine.

The term "aryl" means any stable single, double or more carbon cycles that contains up to 7 atoms, wherein at least one cycle is aryl cycle. When the aryl is double or more cycles substituent group and one or more cycles of them are non-aromatic cycles, the link with the central molecular is done by means of aryl cycle.

Wherein, the said pharmaceutically acceptable salt thereof is preferably the salt that is formed by the reaction of ester and inorganic base or organic base, wherein the said ester is formed by the reaction of 9,10-anthraquinone compound as shown in Formula I and organic acid or acidic amino acid; or the salt that is formed by the reaction of ester and acid, wherein the said ester is formed by the reaction of 9,10-anthraquinone compound as shown in Formula I and basic amino acid.

The said organic acid is preferably propionic acid, oxalic acid or propanedioic acid; the said acidic amino acid is preferably asparaginic acid or glutamic acid; the said salt that is formed with inorganic base or organic base is preferably sodium salt, potassium salt, ammonium salt, methylamine salt or ethamine salt; the said basic amino acid is preferably lysine, arginine or ornithin; the said acid is preferably inorganic acid such as hydrochloric acid, sulphuric acid, nitric acid or phosphoric acid et al. or organic acid such as formic acid, acetic acid or methyl sulfonic acid et al.

In this invention, it was found by study that the 9,10-anthraquinone compound as shown in Formula I, wherein $Y^1$ and $Y^2$ are hydroxyl, and $R^1$, $R^3$, $R^4$ and $R^6$ are all hydrogen, namely the anthraquinone compound having the nuclear parent as shown in Formula A or plant extract containing the said compound has preferable anti-HCV effect.

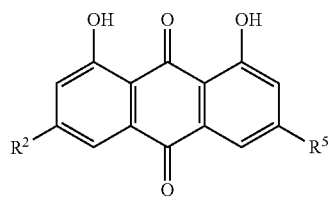

Formula A

Wherein, $R^2$ is H or $CH_3$, $R^5$ is H, OH, $OCH_3$, $OC_2H_5$, COOH, $COOCH_3$, $COOC_2H_5$ or $CH_2OH$.

In this invention, the said anthraquinone compound as shown in Formula A is more preferably selected from the following 5 compounds:

(1) Emodin as shown in Formula B, namely the compound as shown in Formula A, wherein $R^2$ is $CH_3$ and $R^5$ is OH, and the molecular formula thereof is $C_{15}H_{10}O_5$; the molecular weight thereof is 270:25; the chemical name thereof is 1,3,8-dihydroxyl-6-methyl anthraquinone; the English name thereof is Emodin; CAS number thereof is 518-82-1.

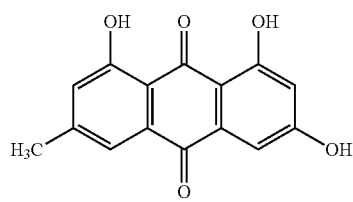

Formula B (2) Chrysophanic acid as shown in Formula C, namely the compound as shown in Formula A, wherein $R^2$ is $CH_3$ and $R^5$ is H, and the molecular formula thereof is $C_{15}H_{10}O_4$; the molecular weight thereof is 254.24; the chemical name thereof is 1,8-dihydroxyl-6-methyl anthraquinone; the English name thereof is Chrysophanic acid; CAS number thereof is 418-74-3.

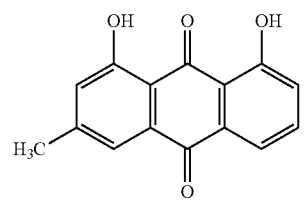

Formula C (3) Physcion as shown in Formula D, namely the compound as shown in Formula A, wherein $R^2$ is $CH_3$ and $R^5$ is $OCH_3$, and the molecular formula thereof is $C_{16}H_{12}O_5$; the molecular weight thereof is 284.27; the chemical name thereof is 1,8-dihydroxyl-3-methoxy-6-methyl anthraquinone; the English name thereof is Physcion; CAS number thereof is 521-61-9.

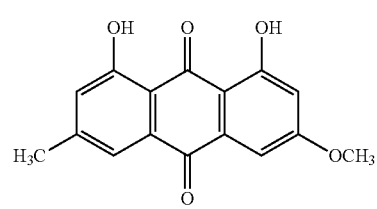

Formula D (4) Aloe-emodin as shown in Formula E, namely the compound as shown in Formula A, wherein $R^2$ is H and $R^5$ is $CH_2OH$, and the molecular formula thereof is $C_{15}H_{10}O_5$; the molecular weight thereof is 270.24; the chemical name thereof is 1,8-dihydroxyl-3-hydroxymethyl anthraquinone; the English name thereof is Aloe-emodin; CAS number thereof is 481-72-1.

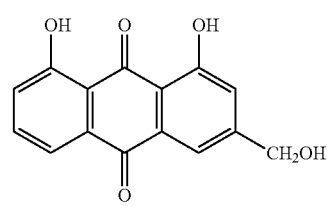

Formula E (5) Rhein as shown in Formula F, namely the compound as shown in Formula A, wherein $R^2$ is H and $R^5$ is COOH, and the molecular formula thereof is $C_{15}H_8O_6$; the molecular weight thereof is 284.22; the chemical name thereof is 1,8-dihydroxyl-3-carboxyl anthraquinone; the English name thereof is Rhein; CAS number thereof is 478-43-3.

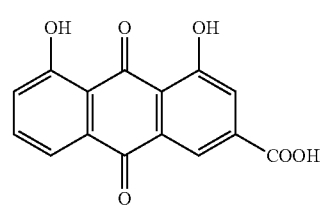

Formula F (6) Danthron as shown in Formula G, namely the compound as shown in Formula A, wherein $R^2$ and $R^5$ are H, and the molecular formula thereof is $C_{14}H_8O_4$; the molecular weight thereof is 240.2; the chemical name thereof is 1,8-dihydroxyl-9,10-anthraquinone; the English name thereof is 1,8-dihydroxyanthroquinone.

Formula G

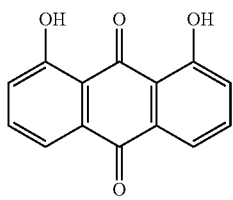

in this invention, it was found by study that the 9,10-anthraquinone compound as shown in Formula I, wherein $Y^1$ is hydrogen and $Y^2$ is hydroxyl; $R^1$ and $R^2$ are hydrogen; $R^3$ is methoxyl; $R^4$ is hydroxyl; $R^5$ and $R^6$ form a ring as shown in Formula IV, namely the anthraquinone compound as shown in Formula A is daunorubicin as shown in Formula J or plant extract containing the said compound has preferable anti-HCV effect. The molecular formula of daunorubicin as shown in Formula J is $C_{27}H_{29}NO_{10}.HCl$; the molecular weight thereof is 564; the chemical name thereof is 5,10-naphthacenequinone, 8-acetyl-10-[(3-amino-2,3,6-trideoxy-a-L-lyxosylpyranyl)-oxy]-7,8,9,10-tetrahydro-6,8,11-trihydroxy-1-methoxyl hydrochloride; the English name thereof is Daunorubicin Hydrochloride.

Formula J

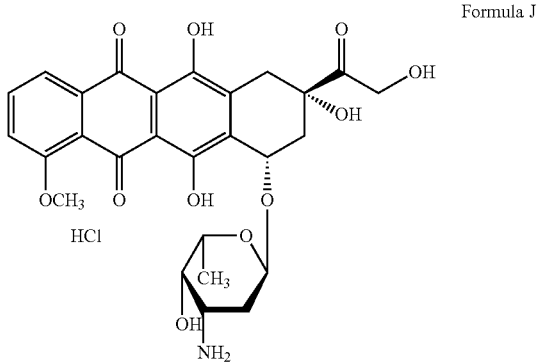

In this invention, it was found by study that the 9,10-anthraquinone compound as shown in Formula I, wherein $Y^1$ is hydrogen and $Y^2$ is hydroxyl; $R^1$, $R^2$, $R^3$, $R^4$ and $R^5$ are hydrogen; $R^6$ is hydroxyl, namely the anthraquinone compound as shown in Formula A is alizarin as shown in Formula K or plant extract containing the said compound has preferable anti-HCV effect. The molecular formula of alizarin as shown in Formula K is $C_{14}H_8O_4$; the molecular weight thereof is 240.2; the chemical name thereof is 1,2-dihydroxyl-9,10-anthraquinone; the English name thereof is Alizarin.

Formula K

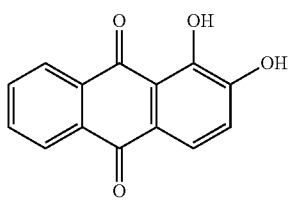

In this invention, it was found by study that the 9,10-anthraquinone compound as shown in Formula I; wherein $Y^1$ is hydrogen; $Y^2$ is hydroxyl; $R^1$, $R^2$, $R^3$ and $R^4$ are hydrogen; $R^5$ is the group as shown in Formula III; $R^6$ is hydroxyl, namely the anthraquinone compound as shown in Formula A is alizarin red S as shown in Formula L or plant extract containing the said compound has preferable anti-HCV effect. The molecular formula of alizarin red S as shown in Formula L is $C_{14}H_7NaO_7S.H_2O$; the molecular weight thereof is 360.3; the chemical name thereof is 1,2-dihydroxylanthraquinone-3-sulfonate; the English name thereof is Alizarin Red S.

Formula L

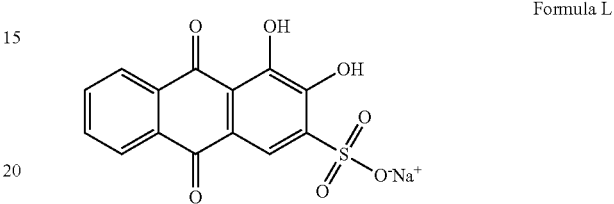

In this invention, it was found by study that the 9,10-anthraquinone compound as shown in Formula I, wherein $Y^1$ is hydrogen; $Y^2$ is hydroxyl; $R^1$, $R^2$, $R^3$, $R^5$ and $R^6$ are hydrogen; $R^4$ is hydroxyl, namely the anthraquinone compound as shown in Formula A is quinizarin as shown in Formula M or plant extract containing the said compound has preferable anti-HCV effect. The molecular formula of quinizarin as shown in Formula M is $C_{14}H_8O_4$; the molecular weight thereof is 240.2; the chemical name thereof is 1,4-dihydroxyl-9,10-anthraquinone; the English name thereof is 1,4-dihydroxyanthroquinone.

Formula M

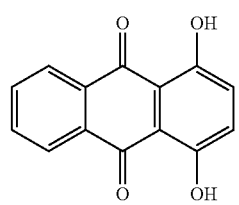

In this invention, it was found by study that the 9,10-anthraquinione compound as shown in Formula I, wherein $Y^1$, $Y^2$, $R^1$, $R^2$, $R^3$, $R^4$, $R^5$ and $R^6$ are hydrogen, namely the anthraquinone compound as shown in Formula A is anthraquinone as shown in Formula N or plant extract containing the said compound has preferable anti-HCV effect. The molecular formula of anthraquinone as shown in Formula N is $C_{14}H_8O_2$; the molecular weight thereof is 208; the chemical name thereof is 9,10-anthraquinone; the English name thereof is Anthraquinone.

Formula N

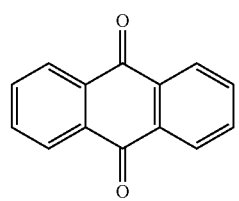

In this invention, it was found by study that the 9,10-anthraquinone compound as shown in Formula I, wherein $Y^1$ is the group as shown in Formula II; $Y^2$ is hydroxyl; $R^1$, $R^3$, $R^4$ and $R^6$ are hydrogen; $R^2$ is methyl, $R^5$ is methoxyl, namely the anthraquinone compound as shown in Formula A is physcion-8-O-β-D-glucoside as shown in Formula Q or plant extract containing the said compound has preferable anti-HCV effect. The molecular formula of physcion-8-O-β-D-glucoside as shown in Formula Q is $C_{22}H_{22}O_{10}$; the molecular weight thereof is 446; the chemical name thereof is physcion-8-O-β-D-glucoside.

Formula Q

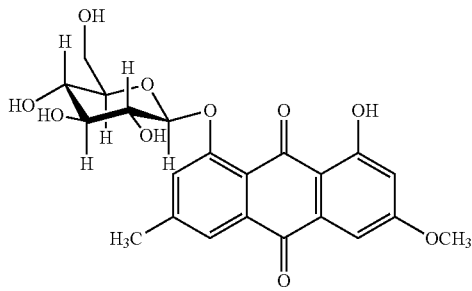

In this invention, it was found by study that the 9,10-anthraquinone compound as shown in Formula I, wherein $Y^1$ is the group as shown in Formula II; $Y^2$ is hydroxyl; $R^1$, $R^3$, $R^4$ and $R^6$ are hydrogen; $R^2$ is methyl; $R^5$ is hydroxyl, namely the anthraquinone compound as shown in Formula A is emodin-8-O-β-D-glucoside as shown in Formula T or plant extract containing the said compound has preferable anti-HCV effect. The molecular formula of emodin-8-O-β-D-glucoside as shown in Formula T is $C_{21}H_{20}O_{10}$; the molecular weight thereof is 432; the chemical name thereof is emodin-8-O-β-D-glucoside.

Formula T

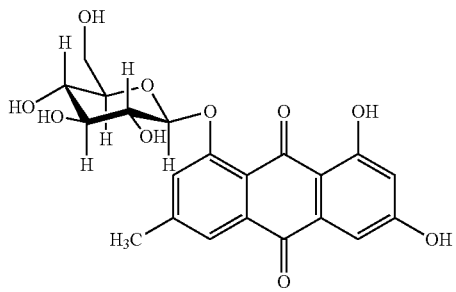

In this invention, the said anthraquinone compound is preferably obtained from natural plant (such as rheum officinale etc.) by extraction and separation. It may be not only the single pure products commercially available, but also the crude or pure product extracted from natural plant. It also may be the plant extract that contains the said anthraquinone compound as effective component. The extract is more preferably the one that is obtained from chinese medicinal material of rhubarb, semen cassiae torae, madder, aloe or folium sennae using one or more solvent/solvents selected from the group consisting of acetone, methanol, ethanol, n-butanol, ethyl acetate, petroleum ether, chloroform, methylene chloride and water.

All the raw materials and reagents in this invention are commercially available.

The active and progressive effects of this invention are: the said anthraquinone compounds in this invention have excellent anti-HCV effect; the side effects are little; they are derived from Chinese herb medicine and are low-priced, safe and effective.

SPECIFIC MODE FOR CARRYING OUT THE INVENTION OR UTILITY MODEL

The following examples are given as a non-limiting illustration of the invention.

The emodin, chrysophanic acid, physcion, apigenin, aloe-emodin, daunorubicin, 1,8-dihydroxyl-9,10-anthraquinone, alizarin, alizarin red S, 1,4-dihydroxyl-9,10-anthraquinone, anthraquinone, physcion-8-O-β-D-glucoside, emodin-8-O-β-D-glucoside and rhein used in the examples were bought from Shanghai Research and Development Centre for Standardization of Chinese Medicine. The HCV-E2 antibody was from the Scripps Research Institute in the United States of America. The control drug interferon-α and other reagents and materials used are commercially available in China.

The extracts of rheum officinale, semen cassiae torae, madder, aloe and folium sennae were the extracts of water or aqueous solution of ethanol with a concentration of 75% (V/V) and the extracts were made by ourselves.

Two portions of the medicinal materials of rheum officinale, semen cassiae torae, madder, aloe and folium sennae, one kilogram each portion, were taken and respectively extracted with water (5 kg) and aqueous solution of ethanol with a concentration of 75% (V/V) (5 Kg), then were concentrated to dryness. After that the extracts were obtained.

The Examples of Cell Experiments In Vitro

1. Preparation of Samples

The stock solutions with a concentration of 20 mg/ml were prepared by dissolving the samples in DMSO and were kept at 4° C. When testing, the stored stock solutions were diluted to 5 mg/ml and 2 mg/ml with DMSO.

2. The Cells, the Virus and the Culture of Cells

The derivative cell line of Huh7 and the virus strain of HCV were used in this experiment. The virus strain can produce high-titer and infectious virus particles of HCV in the cells.

The cells were inoculated in 96-well flat-bottomed plates at a concentration of $1 \times 10^4/100$ μl/well and cultivated overnight. The HCV supernatant was diluted to $1 \times 10^3$ ffu/ml with complete medium (DMEM contains 10% fetal bovine serum, 100 U/ml penicillin and 100 μg/ml streptomycin) and infected the cells at 50 ffu/well.

3. Focus Reduction Assay of HCV Infection

The sample solutions with different concentrations (2 mg/ml and 1 mg/ml) were respectively diluted in complete medium at a volume ratio of 1:50 to reach the concentrations of 40 μg/ml and 20 μg/ml. Appropriate amount of the sample solutions were sucked up respectively and mixed well with equal volume of diluted virus solution to prepare samples with concentrations of 20 μg/ml and 10 μg/ml. After 1 hour of incubation at room temperature, the culture medium in the 96-well flat-bottomed plates was discarded, then 100 μl of the above mixed solution was added to each well, and then was cultured for 8 hours in 37° C. incubator containing 5% $CO_2$. After that, the supernatant was discarded, then was washed once with phosphate buffer without calcium or magnesium ion (DPBS). 150 μl of fresh complete medium was added to each well, and then was cultured for 64 hours in 37° C. incubator containing 5% $CO_2$. 150 μl of 4% paraformaldehyde (PFA) was added to each well, and was fixed at room temperature for 15 min. The supernatant was discarded, then was washed with DPBS for 3 times, and Immune fluorescence staining was conducted with anti HCV-E2 human monoclonal antibody and anti-human secondary antibody labeled by immunofluorescein, then was watched with fluorescence microscope and the amounts of virus colony were recorded.

4. Setting the Negative Control Group

In the negative control group, DMSO was used instead of the sample solutions, and other conditions were the same as that in sample testing.

5. Setting the Control Group of Interferon-α

The solution of the interferon was diluted to 5, 50 and 500 IU/ml respectively with complete medium, and were hatched for 1 hour with cells, then diluted virus solution was added. Other conditions were the same as that in the extract testing.

The inhibition rate=(the amount of virus colony in the negative control group−the amount of virus-colony in the experimental group)/the amount of virus colony in the negative control group×100%.

Experimental Results

| Sample | Concentration of compound μg/ml | Cytotoxicity | Inhibition Rate of the number of Virus foci (%) |
| --- | --- | --- | --- |
| Emodin | 20 | None | 99% |
|  | 10 | None | 79% |
|  | 5 | None | 52% |
| Chrysophanic acid | 20 | None | 48% |
|  | 10 | None | 17% |
|  | 5 | None | 21% |
| Physcion | 20 | None | 100% |
|  | 5 | None | 100% |
| Aloe-emodin | 20 | None | 100% |
|  | 5 | None | 95% |
| Rhein | 20 | None | 82% |
|  | 5 | None | 44% |
| Daunorubicin | 0.04 | None | 57% |
| 1,8-Dihydroxyl-9,10-anthraquinone | 0.04 | None | 45% |
|  | 0.2 | None | 100% |
| Alizarin | 10 | None | 31% |
| Alizarin Red S | 10 | None | 22% |
| 1,4-dihydroxyl-9,10-anthraquinone | 5 | None | 81% |
| Anthraquinone | 5 | None | 44% |
| Physcion-8-O-β-D-glucoside | 100 | None | 40% |
| Emodin-8-O-β-D-glucoside | 100 | None | 40% |
| The extracts of rheum officinale of 75% (V/V) ethanol aqueous solution | 20 | None | 95% |
|  | 5 | None | 83% |
| The extracts of rheum officinale of water | 20 | None | 76% |
|  | 5 | None | 53% |
| The extracts of folium sennae of 75% (V/V) ethanol aqueous solution | 20 | None | 98% |
|  | 5 | None | 47% |
| The extracts of aloe of 75% (V/V) ethanol aqueous solution | 20 | None | 84% |
|  | 5 | None | 38% |
| The extracts of semen cassiae torae of 75% (V/V) ethanol aqueous solution | 20 | None | 80% |
|  | 5 | None | 50% |
| The extracts of madder of 75% (V/V) ethanol aqueous solution | 20 | None | 89% |
|  | 5 | None | 47% |
| Apigenin | 20 | None | 47% |
|  | 5 | None | 11% |
| The Negative Control Group | \ | None | 0% |
| The Control Group of α-interferon | 500 IU/ml | None | 98% |
|  | 50 IU/ml | None | 79% |
|  | 5 IU/ml | None | 53% |

The tests showed that the IC$_{50}$ of physcion was 8 ng/ml, and its activity was better than other compounds.

Instructions to Cytotoxicity:

Noncytotoxic=the cell density of the experimental group/the cell density of the negative control group≤80%

Cytotoxicity=the cell density of the experimental group/the cell density of the negative control group<80%

The experimental results show that the anthraquinone compounds, such as physcion, emodin, aloe-emodin, rhein, daunorubicin, 1,8-dihydroxyl-9,10-anthraquinone, alizarin, alizarin red S, 1,4-dihydroxyl-9,10-anthraquinone, anthraquinone, physcion-8-O-β-D-glucoside, emodin-8-O-β-D-glucoside and chrysophanol etc. and the plant extracts of rheum officinale, semen cassiae torae, madder, aloe and folium sennae have obvious inhibition effect towards HCV.

In conclusion, each experimental result shows that physcion, chrysophanol, emodin, aloe-emodin, daunorubicin, 1,8-dihydroxyl-9,10-anthraquinone, alizarin, alizarin red S, 1,4-dihydroxyl-9,10-anthraquinone, anthraquinone, physcion-8-O-β-D-glucoside, emodin-8-O-β-D-glucoside, rhein and the plant extracts containing them all have anti-HCV effect, wherein, physcion is the best.

What is claimed is:

1. A method of treating a patient in need of a medicament for anti-hepatitis C virus, comprising administering to the patient a medicament comprising an effective amount of a 9,10-anthraquinone of Formula I:

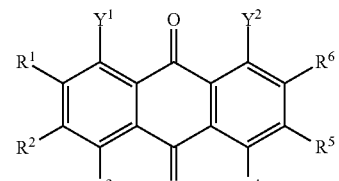

Formula I

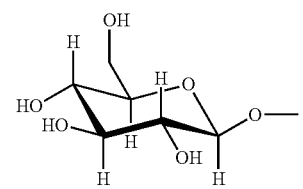

Formula II

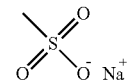

Formula III

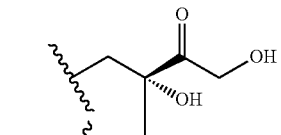

Formula IV

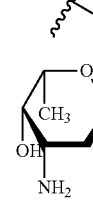

or a pharmaceutically acceptable salt thereof or a plant extract thereof:

wherein $Y^1$ and $Y^2$ are independently hydrogen, hydroxyl or a group as shown in Formula II; $R^1$, $R^2$, $R^3$, $R^4$, $R^5$, and $R^6$, are independently hydrogen, hydroxyl, carboxyl, cyano, nitryl, a group as shown in Formula III or one of the following groups with one or more substituent groups or unsubstituted; amino, $C_1$~$C_6$ chain hydrocarbyl, $C_3$~$C_7$ cyclic aliphatic hydrocarbyl, $C_1$~$C_6$ alkoxy, $C_2$~$C_7$ alkoxy carbonyl, $C_1$~$C_4$ acyloxy, $C_6$~$C_{20}$ aryl or 5~7 members heterocyclic ring or benzohetercyclic ring thereof, wherein the one or more substituent groups are one or more selected from the group consisting of halogen, $C_1$~$C_6$ chain hydrocarbyl, cyano, nitryl, amino, hydroxyl, carboxyl, $C_1$~$C_4$ alkoxy, mercapto, $C_1$~$C_4$ acyloxy and $C_6$~$C_{20}$ aryl; or $R^5$ and $R^6$ form a ring as shown in Formula IV, with the proviso that the 9,10-anthraquinone of formula I excludes emodin, aloe-emodin, and daunorubicin.

2. The method according to claim 1, wherein the $C_6$~$C_{20}$ aryl is phenyl, naphthyl, tetrahydro naphthyl, 2,3-dihydro indenyl, diphenyl, phenanthryl, anthryl or acenaphthenyl; the 5~7 members heterocyclic ring is the one that contains 1~3 hetero atom/atoms selected from the group consisting of oxygen, sulfur and nitrogen.

3. The method according to claim 1, wherein the $R^1$, $R^2$, $R^3$, $R^4$, $R^5$ and $R^6$ are independently H, $CH_3$, OH, $OCH_3$, $OC_2H_5$, COOH, $COOCH_3$, $COOC_2H_5$, $CH_2OH$, trifluoromethyl, trifluoromethoxy or benzyl.

4. The method according to claim 1, wherein the pharmaceutically acceptable salt is the one formed by the reaction of ester and inorganic base or organic base, wherein the ester is formed by the reaction of 9,10-anthraquinone compound as shown in Formula I and organic acid or acidic amino acid; or the one that is formed by the reaction of ester and acid, wherein the ester is formed by the reaction of 9,10-anthraquinone compound as shown in Formula I and basic amino acid.

5. The method according to claim 4, wherein the organic acid is propionic acid, oxalic acid or propanedioic acid; the acidic amino acid is asparaginic acid or glutamic acid; the salt formed with inorganic base or organic base is sodium salt, potassium salt, ammonium salt, methylamine salt or ethamine salt; the basic amino acid is lysine, arginine or ornithin; the acid is hydrochloric acid, sulphuric acid, nitric acid, phosphoric acid, formic acid, acetic acid or methyl sulfonic acid.

6. The method according to claim 1, wherein $Y^1$ and $Y^2$ are hydroxyl;
$R^1$, $R^3$, $R^4$ and $R^6$ are hydrogen; namely the compound as shown in Formula I is the anthraquinone compound as shown in Formula A or plant extract containing the compound;

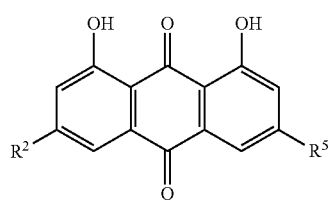

Formula A

Wherein, $R^2$ is H or $CH_3$, $R^5$ is H, OH, $OCH_3$, $OC_2H_5$, COOH, $COOCH_3$, $COOC_2H_5$ or $CH_2OH$.

7. The method according to claim 6, wherein
$R^2$ is $CH_3$ and $R^5$ is H; namely the anthraquinone compound as shown in Formula A is chrysophanic acid as shown in Formula C:

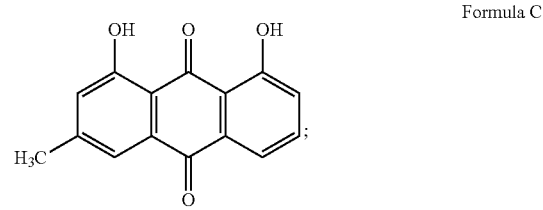 [SMILES: Cc1cc(O)c2c(c1)C(=O)c1cccc(O)c1C2=O]

Formula C

Or $R^2$ is $CH_3$ and $R^5$ is $OCH_3$; namely the anthraquinone compound as shown in Formula A is physcion as shown in Formula D:

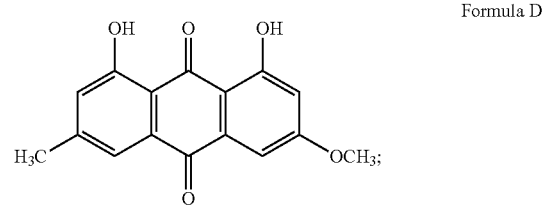 [SMILES: COc1cc(O)c2c(c1)C(=O)c1cc(C)cc(O)c1C2=O]

Formula D

Or $R^2$ is H and $R^5$ is COOH; namely the anthraquinone compound as shown in Formula A is rhein as shown in Formula F:

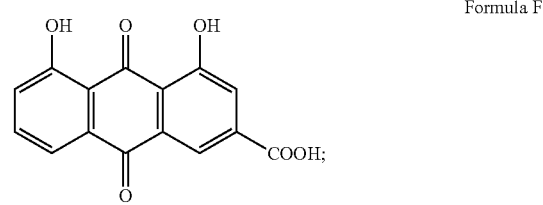 [SMILES: O=C(O)c1cc(O)c2c(c1)C(=O)c1cccc(O)c1C2=O]

Formula F

Or $R^2$ and $R^5$ are H; namely the anthraquinone compound as shown in Formula A is danthron as shown in Formula G;

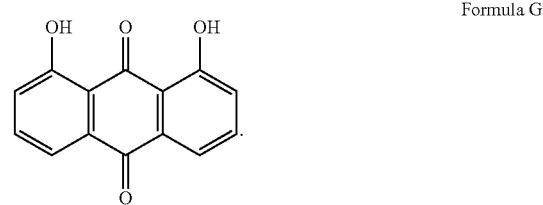 [SMILES: O=C1c2cccc(O)c2C(=O)c2c(O)cccc21]

Formula G

8. The method according to claim 1, wherein $Y^1$ is hydrogen; $Y^2$ is hydroxyl; $R^1$, $R^2$, $R^3$, $R^4$ and $R^5$ are hydrogen; $R^6$ is hydroxyl; namely the anthraquinone compound as shown in Formula I is alizarin as shown in Formula K;

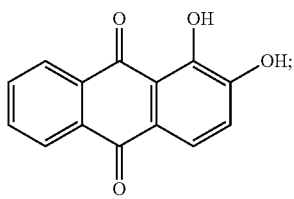
Formula K

Or $Y^1$ is hydrogen; $Y^2$ is hydroxyl; $R^1$, $R^2$, $R^3$ and $R^4$ are hydrogen; $R^5$ is the group as shown in Formula III; $R^6$ is hydroxyl: namely the anthraquinone compound as shown in Formula I is alizarin red S as shown in Formula L;

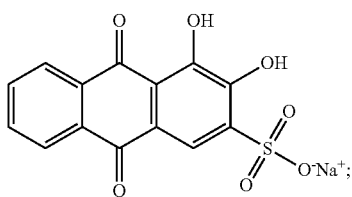
Formula L

Or $Y^1$ is hydrogen; $Y^2$ is hydroxyl; $R^1$, $R^2$, $R^3$, $R^5$ and $R^6$ are hydrogen; $R^4$ is hydroxyl; namely the anthraquinone compound as shown in Formula I is quinizarin as shown in Formula M;

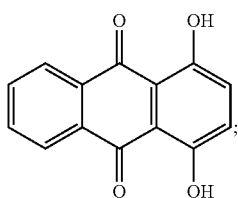
Formula M

Or $Y^1$, $Y^2$, $R^1$, $R^2$, $R^3$, $R^4$, $R^5$ and $R^6$ are hydrogen; namely the anthraquinone compound as shown in Formula I is anthraquinone as shown in Formula N:

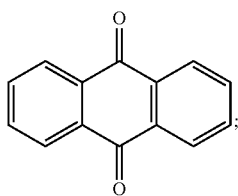
Formula N

Or $Y^1$ is the group in Formula II; $Y^2$ is hydroxyl; $R^1$, $R^3$, $R^4$ and $R^6$ are hydrogen; $R^2$ is methyl; $R^5$ is methoxyl, namely the anthraquinone compound as shown in Formula I is physcion-8-O-β-D-glucoside as shown in Formula Q;

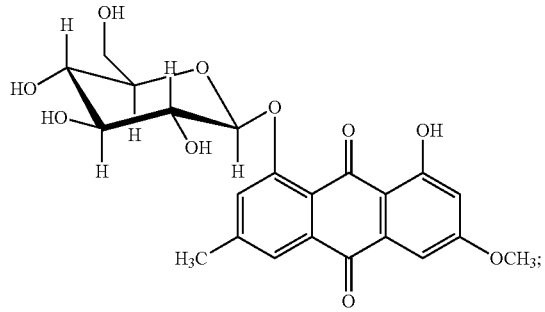
Formula Q

Or $Y^1$ is the group in Formula II; $Y^2$ is hydroxyl; $R^1$, $R^3$, $R^4$ and $R^6$ are hydrogen; $R^2$ is methyl; $R^5$ is hydroxyl, namely the anthraquinone compound as shown in Formula I is emodin-8-O-β-D-glucoside as shown in Formula T;

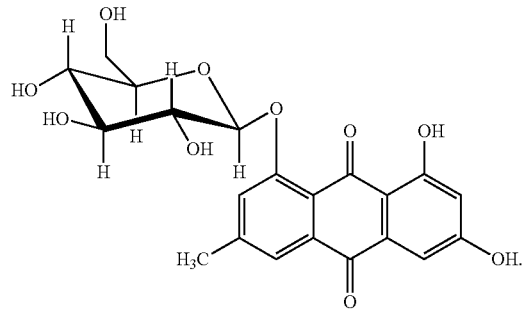
Formula T

9. The method according to claim 1, the plant extract is the one that is extracted from rhubarb, folium sennae, semen cassiae torae, aloe or madder with one or more solvent/solvents selected from the group consisting of acetone, methanol, ethanol, n-butanol, ethyl acetate, petroleum ether, chloroform, methylene chloride and water.

10. The method according to claim 1, wherein the patient in need of a medicament for anti-hepatitis C virus is in need of a medicament for treatment of viral hepatitis C.

11. A method of treating a patient in need of a medicament for anti-hepatitis C virus, comprising administering to the patient a medicament comprising an effective amount of a 9,10-anthraquinone of formula I;

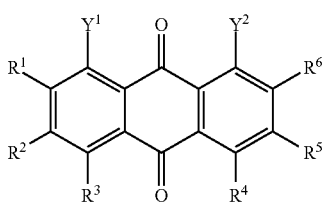
Formula I or a pharmaceutically acceptable salt thereof or a plant extract thereof;

Wherein, $Y^1$ and $Y^2$ are hydroxyl;

$R^1$, $R^2$, $R^3$, $R^4$, $R^5$ and $R^6$ are independently hydrogen, hydroxyl, carboxyl, cyano, nitryl, or one of the following groups with one or more substituent groups or unsubstituted: amino, $C_1$~$C_6$ chain hydrocarbyl, $C_3$~$C_7$ cyclic aliphatic hydrocarbyl, $C_1$~$C_6$ alkoxy, $C_2$~$C_7$ alkoxy carbonyl, $C_1$~$C_4$ acyloxy, $C_6$~$C_{20}$ aryl or 5~7 members heterocyclic ring or benzohetercyclic ring thereof, wherein the one or more substituent groups are one or more selected from the group consisting of halogen, $C_1$~$C_6$ chain hydrocarbyl, cyano, nitryl, amino, hydroxyl, carboxyl, $C_1$~$C_4$ alkoxy, mercapto, $C_1$~$C_4$ acyloxy and $C_6$~$C_{20}$ aryl.

12. The method according to claim 11, wherein the patient in need of a medicament for anti-hepatitis C virus is in need of a medicament for treatment of viral hepatitis C.

* * * * *